US006638530B1

United States Patent
Ishibashi et al.

(10) Patent No.: US 6,638,530 B1
(45) Date of Patent: Oct. 28, 2003

(54) BENZAMIDE FORMULATION WITH HISTONE DEACETYLASE INHIBITOR ACTIVITY

(75) Inventors: Masahiko Ishibashi, Mobara (JP); Masahiro Sakabe, Mobara (JP); Ikuo Sakai, Mobara (JP); Tsuneji Suzuki, Mobara (JP); Tomoyuki Ando, Mobara (JP)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/069,582

(22) PCT Filed: Aug. 29, 2000

(86) PCT No.: PCT/EP00/08421

§ 371 (c)(1),
(2), (4) Date: Feb. 27, 2002

(87) PCT Pub. No.: WO01/16106

PCT Pub. Date: Mar. 8, 2001

(30) Foreign Application Priority Data

Aug. 30, 1999 (JP) .......................................... 11-242444

(51) Int. Cl.$^7$ ............................ A61K 9/66; A61K 31/44
(52) U.S. Cl. ........................ 424/455; 514/351; 514/352
(58) Field of Search ................................ 514/351, 352; 424/455

(56) References Cited

U.S. PATENT DOCUMENTS 6,218,410 B1 * 4/2001 Uehata et al. ............... 514/241

FOREIGN PATENT DOCUMENTS

EP 0 847 992 A1 6/1998
EP 11-302173 11/1999
JP 11-302173 11/1999

OTHER PUBLICATIONS

Database WPI, Section Ch, Week 200064, Derwent Publications Ltd., London, GB.
Japan 2000 256194 A (Mitsui Chem Inc.), Sep. 19, 2000 (abstract).
Tsuneji Suzuki, "Synthesis and Histone Deacetylase Inhibitory Activity of New Benzamide Derivatives", J. Med. Chem. (1999), 42(15), pp. 3001–3003.
Akiko Saito et al., "A Synthetic Inhibitor of Histone Deacetylase, MS–27–275, With Marked in vivo Antitumor Activity Against Human Tumors", Proc. Natl. Acad. Sci. U.S.A. (1999), 96(8), pp. 4592–4597.

* cited by examiner

Primary Examiner—James H Reamer
(74) Attorney, Agent, or Firm—Morgan, Lewis & Bockius LLP

(57) ABSTRACT

There are provided pharmaceutical formulations with improved oral absorptivity and injections that contain, as active ingredients, high concentrations of benzamide derivatives and their pharmaceutically acceptable salts, which are useful as histone deacetylase inhibitors.

A pharmaceutical solution is prepared by dissolving a benzamide derivative or a pharmaceutically acceptable salt thereof in an organic solvent and/or acidic liquid, and a pharmaceutical formulation is prepared by adding a surfactant, an acidic substance and/or a polyethylene glycol.

The present invention has enabled dissolution of benzamide derivatives or their pharmaceutically acceptable salts at high concentrations, to prepare practical injections and oral liquid formulations and improve absorptivity with oral administration.

9 Claims, 1 Drawing Sheet

BENZAMIDE FORMULATION WITH HISTONE DEACETYLASE INHIBITOR ACTIVITY

This application is a 371 of PCT/EP00/08421 filed Aug. 29, 2002.

FIELD OF THE INVENTION

The present invention relates a pharmaceutical formulation with increased solubility containing benzamide derivative or a pharmaceutically acceptable salt thereof, which are useful as drugs, and especially anticancer drugs. In particular, it relates to a pharmaceutical formulation containing high concentration of active ingredient with improved oral absorptivity, that may also be used as injection.

BACKGROUND ART

The benzamide derivatives used for the invention and their pharmaceutically acceptable salts have histone deacetylase inhibitory action, and are useful as therapeutic and/or ameliorating agents for disease connected with cellular growth, as effect enhancers for gene therapy, and as immunosuppressants. They exhibit particularly powerful effects as anticancer agents, and are effective for hematopoietic tissue tumors and solid tumors (Japanese Unexamined Patent Publication HEI No. 10-152462).

However, while the benzamide derivatives used for the invention have very satisfactory absorptivity when orally administered to mice and rats, some cases of low absorptivity have been found in dogs. Some cases of low absorptivity with oral administration have also been found even when the formulations are prepared using common additives such as lactose, corn starch, carboxymethyl cellulose, light anhydrous silicic acid, magnesium aluminometasilicate, magnesium stearate and titanium oxide. It has therefore been considered difficult to achieve stable blood concentration only with formulation for oral administration containing benzamide derivative or salt thereof as an active ingredient.

It has also been attempted to dissolve benzamide derivatives or their pharmaceutically acceptable salts in water, phosphate buffer solution and the like to make liquid drugs or injections, but their low solubility has made it impossible to obtain formulations of sufficient concentration.

Thus, injections containing benzamide derivatives or their salts as active ingredients must have very large volumes because of the poor solubility of the active ingredients, and it has therefore been difficult to provide them as drugs.

DISCLOSURE OF THE INVENTION

It is an object of the present invention to provide formulations with increased solubility and improved oral absorptivity for benzamide derivatives and their pharmaceutically acceptable salts that are useful as histone deacetylase inhibitors, and to provide injections containing the active ingredient at high concentration.

In order to overcome the problems described above, the present inventors have conducted diligent research on addition of various additives to benzamide derivatives and their pharmaceutically acceptable salts to improve solubility and absorptivity, and as a result the present inventors have completed the present invention upon finding that this object can be achieved by using certain types of additives.

In other words, the present invention provides:

[1] A pharmaceutical formulation comprising a benzamide derivative represented by formula (1):

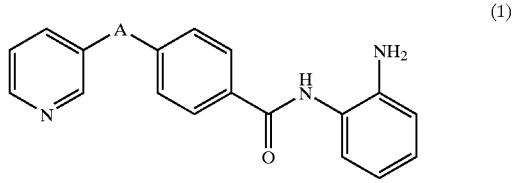

(1)

wherein A represents a structure represented by any one of the following in formula (2):

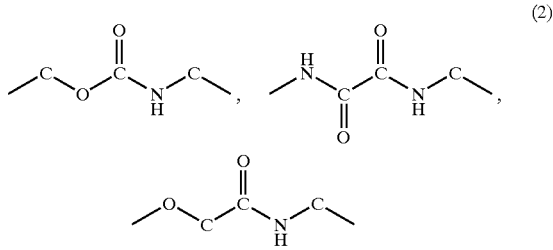

(2)

or a pharmaceutically acceptable salt thereof, and one or more than one selected from the group consisting of surfactants, acidic substances, organic solvents and polyethylene glycols;

[2] The pharmaceutical formulation according to [1] further comprising water;

[3] The pharmaceutical formulation according to [1] or [2] wherein the benzamide derivative is represented by formula (3):

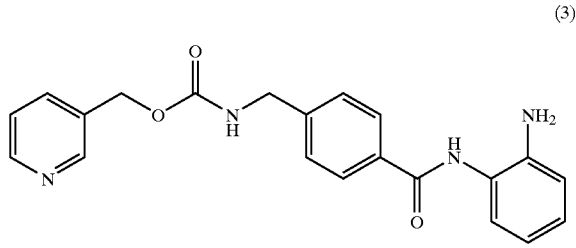

(3)

[4] The pharmaceutical formulation according to any one of [1] to [3] wherein the surfactant is one or two selected from anionic surfactants and nonionic surfactants;

[5] The pharmaceutical formulation according to any one of [1] to [4] wherein the acidic substance is one or more than one selected from the group consisting of mineral acids, carboxylic acids, sulfonic acids, acidic polysaccharides, acidic amino acids, and salts of an amino acid and a mineral acid;

[6] The pharmaceutical formulation according to any one of [1] to [5] wherein the organic solvent is one or more than one selected from the group consisting of methanol, ethanol, propylene glycol, glycerin, propylene carbonate and dimethylacetamide;

[7] The pharmaceutical formulation according to any one of [1] to [6] wherein the molecular weight of the polyethylene glycol is from 200 to 20,000;

[8] The pharmaceutical formulation according to any one of [4] to [7] wherein the anionic surfactant is sodium lauryl sulfate;

[9] The pharmaceutical formulation according to any one of [4] to [8] wherein the nonionic surfactant is a polyoxyethylene sorbitan fatty acid ester or a sugar ester;

[10] The pharmaceutical formulation according to [9] wherein the polyethylene sorbitan fatty acid ester is polysorbate 80;

[11] The pharmaceutical formulation according to [9] wherein the sugar ester is a sucrose ester of fatty acid;

[12] The pharmaceutical formulation according to any one of [5] to [11] wherein the mineral acid is hydrochloric acid, sulfuric acid or phosphoric acid;

[13] The pharmaceutical formulation according to any one of [5] to [11] wherein the carboxylic acid is citric acid, fumaric acid, adipic acid, tartaric acid, malic acid or acetic acid;

[14] The pharmaceutical formulation according to any one of [5] to [11] wherein the sulfonic acid is aminoethylsulfonic acid;

[15] The pharmaceutical formulation according to any one of [5] to [11] wherein the acidic polysaccharide is alginic acid;

[16] The pharmaceutical formulation according to any one of [5] to [11] wherein the acidic amino acid is aspartic acid or glutamic acid;

[17] The pharmaceutical formulation according to any one of [5] to [11] wherein the salt of an amino acid and a mineral acid is glycine hydrochloride, aspartic acid hydrochloride or glutamic acid hydrochloride.

EMBODIMENT FOR CARRYING OUT THE INVENTION

Figure 1:
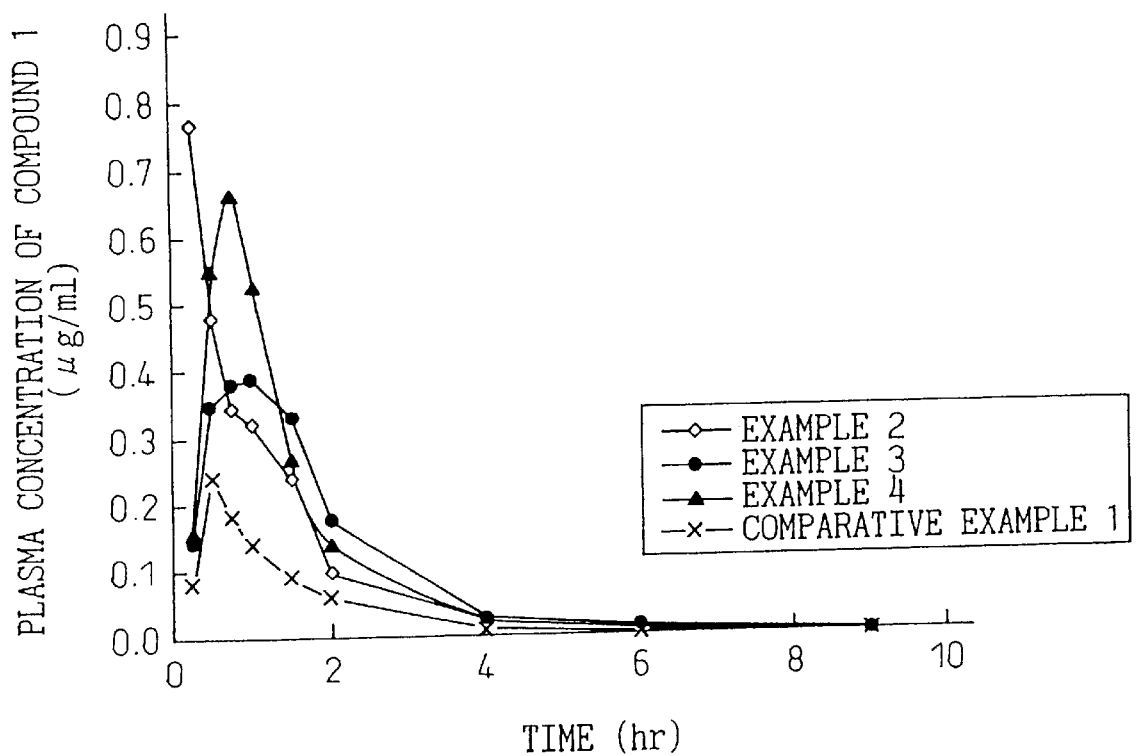
FIG. 1 shows serial changes in plasma concentrations upon oral administration of the formulations obtained in Examples 2 to 4 and Comparative Example 1 to fasted male beagles with 20 ml of water.

The present invention will now be explained in greater detail. Formulations are generally produced by including one or more additives to the active ingredient.

The benzamide derivatives as active ingredients for formulations, as represented by formula (1) according to the invention, are exemplified in Table 1, and these compounds may be produced by the process described in, for example, Japanese Unexamined Patent Publication HEI No. 10-152462.

TABLE 1

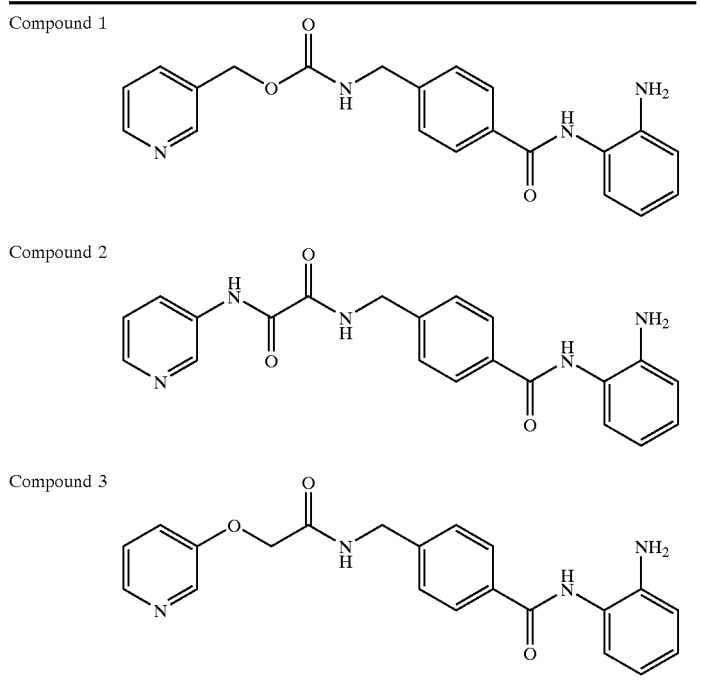

Surfactants to be used for the invention include anionic surfactants, cationic surfactants, nonionic surfactants, amphoteric surfactants and the like without particular restrictions; and sodium lauryl sulfate, polysorbate 80, sucrose ester of fatty acid and the like are preferably used alone or in combination.

Acidic substances to be used for the invention include mineral acids such as hydrochloric acid, sulfuric acid and phosphoric acid; carboxylic acids such as acetic acid, lactic acid, fumaric acid, tartaric acid, succinic acid, citric acid, oxalic acid, malonic acid, maleic acid, dl-malic acid, stearic acid and adipic acid; sulfonic acids such as aminoethylsulfonic acid; acidic polysaccharides such as alginic acid; acidic amino acids such as glutamic acid and aspartic acid; and salts of an amino acid and a mineral acid, such as glycine hydrochloride, aspartic acid hydrochloride and glutamic acid hydrochloride.

One or more than one acidic substance(s) can be used for the present invention.

These acidic substances may be formulated with the active ingredient together with a surfactant, an organic solvent, a polyethylene glycol and/or the like, but they may also be used as a solution in water.

Organic solvents to be used for the invention include methanol, ethanol, propylene glycol, glycerin, dimethylformamide and propylene carbonate, and one or more than one of these may be used, optionally in the form of a solution in water.

The polyethylene glycol used for the invention is not particularly restricted in terms of its molecular weight, but it preferably has a molecular weight in the range of 200 to 20,000, and more preferably in the range of 200 to 600. One or more than one type may be selected for use, optionally in the form of a solution in water.

A soft capsule encapsuling a liquid, a hard capsule encapsuling a liquid and the like according to the present invention may be prepared by dissolving an appropriate amount of a benzamide derivative or its pharmaceutically acceptable salt, (i) in a liquid comprising one or more than one selected from the group consisting of organic solvents, polyethylene glycols and surfactants;

(ii) in a liquid comprising water and one or more than one selected from the group consisting of organic solvents, polyethylene glycols and surfactants;

(iii) in a liquid comprising one or more than one acidic substance(s), water and one or more than one selected from the group consisting of organic solvents, polyethylene glycols and surfactants; or (iv) in a liquid comprising one or more than one acidic substance(s) and water, and making the soft capsule encapsuling a liquid, the hard capsule encapsuling a liquid and the like by a conventional method to those skilled in the art.

The organic solvent which is used for preparing the soft capsules, the hard capsules and the like includes methanol, ethanol, propylene glycol, glycerin, dimethylformamide and propylene carbonate; the polyethylene glycol which is used for preparing the soft capsules, the hard capsules and the like includes polyethylene glycols of molecular weight 200 to 600; the surfactant which is used for preparing the soft capsules, the hard capsules and the like includes polysorbate 80; and the acidic substance which is used for preparing the soft capsules, the hard capsules and the like includes mineral acids such as hydrochloric acid, sulfuric acid and phosphoric acid; carboxylic acids such as acetic acid, lactic acid, fumaric acid, tartaric acid, succinic acid, citric acid, oxalic acid, malonic acid, maleic acid, dl-malic acid, stearic acid and adipic acid; sulfonic acids such as aminoethylsulfonic acid; acidic polysaccharides such as alginic acid; acidic amino acids such as glutamic acid and aspartic acid; and salts of an amino acid and a mineral acid, such as glycine hydrochloride, aspartic acid hydrochloride and glutamic acid hydrochloride According to the invention, a solid formulation such as a powder, granules, tablets, pills and capsules may be prepared by adding to the active ingredient and one or more than one substance selected from the group consisting of surfactants such as sodium lauryl sulfate and sucrose ester of fatty acid; a polyethylene glycol such as polyethylene glycol 4000 and polyethylene glycol 6000; acidic substances including mineral acids such as hydrochloric acid, sulfuric acid and phosphoric acid; carboxylic acids such as acetic acid, lactic acid, fumaric acid, tartaric acid, succinic acid, citric acid, oxalic acid, malonic acid, maleic acid, dl-malic acid, stearic acid and adipic acid; sulfonic acids such as aminoethylsulfonic acid; acidic polysaccharides such as alginic acid; acidic amino acids such as glutamic acid and aspartic acid; and salts of an amino acid and a mineral acid, such as glycine hydrochloride, aspartic acid hydrochloride and glutamic acid hydrochloride, and further using an excipient, binder, disintegrator, lubricant, coating agent or the like for preparation, according to a conventional method to those skilled in the art.

Excipients to be used for the present invention include D-mannitol, lactose, sucrose, corn starch, crystalline cellulose and the like. Binders to be used for the present invention include hydroxypropyl cellulose, polyvinylpyrrolidone, gelatin, glycerin, water and the like.

Disintegrators to be used for the present invention include carmellose, carmellose calcium, sodium carboxymethyl starch, low-substituted hydroxypropyl cellulose, partly pregelatinized starch, and the like. Lubricants to be used for the present invention include magnesium stearate, calcium stearate, and the like.

Coating agents to be used for the present invention include hydroxypropylmethyl cellulose, methacrylic acid copolymers, hydroxypropylmethyl cellulose phthalate, and the like.

The tablets may be tablets that are surrounded with a general coating if necessary, such as sugar-coated tablets, gelatin-encapsulated tablets, enteric-coated tablets or film-coated tablets. Further the tablets can be double-layered or multilayered tablets which have separate layers of the active ingredient, the acidic substance, the surfactant and the like.

An injection according to the present invention may be prepared by dissolving an appropriate amount of a benzamide derivative or its phamaceutically acceptable salt, (i) in a liquid comprising one or more than one selected from the group consisting of organic solvents, polyethylene glycols and surfactants;

(ii) in a liquid comprising water and one or more than one selected from the group consisting of organic solvents, polyethylene glycols and surfactants;

(iii) in a liquid comprising one or more than one acidic substance(s), water and one or more than one selected from the group consisting of organic solvents, polyethylene glycols and surfactants; or (iv) in a liquid comprising one or more than one acidic substance(s) and water, and making the injection by a conventional method to those skilled in the art.

The organic solvent which is used for preparing the injection includes methanol, ethanol, propylene glycol, glycerin, dimethylformamide and propylene carbonate; the polyethylene glycol which is used for preparing the injection includes polyethylene glycols of molecular weight 200 to 600; the surfactant which is used for preparing the injection includes polysorbate 80; and the acidic substance which is used for preparing the injection includes mineral acids such as hydrochloric acid, sulfuric acid and phosphoric acid; carboxylic acids such as acetic acid, lactic acid, fumaric acid, tartaric acid, succinic acid, citric acid, oxalic acid, malonic acid, maleic acid, dl-malic acid, stearic acid and adipic acid; sulfonic acids such as aminoethylsulfonic acid; acidic polysaccharides such as alginic acid; acidic amino acids such as glutamic acid and aspartic acid; and salts of an amino acid and a mineral acid, such as glycine hydrochloride, aspartic acid hydrochloride and glutamic acid hydrochloride.

Alternatively, after dissolving in water the one or more than one selected from the group consisting of these acidic substances, an appropriate amount of a benzamide derivative or its pharmaceutically acceptable salt may be dissolved therein to obtain an injection prepared by a conventional method to those skilled in the art. In this case, a surfactant such as sodium lauryl sulfate and/or a sucrose ester of fatty acid, and/or a polyethylene glycol such as polyethylene glycol 4000 and/or polyethylene glycol 6000 may be used together therewith to improve the solubility of the benzamide derivative.

There are no particular restrictions on the method of administration for the pharmaceutical formulation of the invention, and it may be administered by a method suitable for the preparation form, the age, gender and condition severity of the patient, and other factors. For example, tablets, pills, liquid drugs, syrups, suspensions, emulsions, granules and capsules are administered orally, while injections are administered intravenously either alone or in admixture with a conventional fluid solution comprising glucose, amino acids or the like; if necessary, they are administered intramuscularly, subcutaneously or intraabdominally.

The dose for these pharmaceutical formulations according to the invention may be appropriately selected based on the method of administration, the age, gender and condition severity of the patient and other factors; however, the dose for most active ingredients may be about 0.0001 to 100 mg per day per kilogram of body weight. Amount of the active ingredient per unit dosage form is preferably included in the range of about 0.001 to 1000 mg.

EXAMPLES

The present invention will now be explained in further detail by way of examples and a comparative example. It is to be noted, however, that the present invention is not limited by these examples in any way.

Example 1

After thoroughly blending 100 mg of compound 1 with 10 ml each of 0.05 N hydrochloric acid solution, methanol, ethanol, propylene carbonate, polysorbate 80, polyethylene glycol 400, polyethylene glycol 300, glycerin, dimethylacetamide or propylene glycol at room temperature, the supernatant obtained by centrifugal separation of each mixture was separated off and used as a pharmaceutical solution. Comparative control samples were also prepared by thoroughly dissolving 100 mg of compound 1 with 10 ml each of purified water, sodium acetate buffer solution at pH 4.0 or sodium phosphate buffer solution at pH 6.8 at room temperature, and separating off the supernatant obtained by centrifugal separation. Table 2 shows a result of measuring the concentration of compound 1 in each sample by HPLC analysis. All of the samples of the present invention contained dissolved compound 1 at a concentration of 5 mg/ml or greater, which is a sufficient concentration for an injection. On the other hand, all of the comparative control samples contained dissolved compound 1 only at a concentration of 0.2 mg/ml or less, and therefore the concentration necessary for an injection could not be guaranteed.

TABLE 2

Comparison of solubility of compound 1 in solvent

| Solvent | Compound 1 concentration (mg/ml) |
| --- | --- |
| Comparative Control Samples | |
| water | 0.04 |
| sodium acetate buffer, pH 4.0 | 0.2 |
| phosphate buffer, pH 6.8 | 0.04 |
| Samples of present invention | |
| 0.05 N hydrochloric acid solution | 14.0 |
| methanol | 9.9 |
| ethanol | 5.4 |
| propylene carbonate | 17.5 |
| polysorbate 80 | 29.9 |
| polyethylene glycol 400 | 77.7 |
| polyethylene glycol 300 | 69.1 |

TABLE 2-continued

Comparison of solubility of compound 1 in solvent

| Solvent | Compound 1 concentration (mg/ml) |
| --- | --- |
| glycerin | 10.0 |
| dimethylacetamide | >100 |
| propyleneglycol | 54.6 |

Example 2

10.13 g of polyethylene glycol 400 and 1.08 g of polysorbate 80 and 200 mg of compound 1 were mixed together and, the mixture was completely dissolved by ultrasonic treatment for 30 minutes with occasional mixing. The solution was filled into hard gelatin capsules so that the dosage can be 1.5 mg/kg based on body weight for dogs before administration, to prepare a pharmaceutical formulation.

Example 3

200 mg of compound 1, 700 mg of polyethylene glycol 4000, 800 mg of polyethylene glycol 6000, 600 mg of sodium lauryl sulfate and 1200 mg of sucrose ester of fatty acid were weighed out and mixed in an agate mortar, and the mixture was pulverized with a pestle. The mixed powder was filled into hard gelatin capsules so that the dosage can be 1.5 mg/kg based on body weight for dogs before administration, to prepare a pharmaceutical formulation.

Example 4

200 mg of compound 1, 1350 mg of glutamic acid hydrochloride and 1950 mg of D-mannitol were weighed out and mixed in an agate mortar, and the mixture was pulverized with a pestle. The mixed powder was filled into hard gelatin capsules so that the dosage can be 1.5 mg/kg based on body weight for dogs before administration, to prepare a pharmaceutical formulation.

Comparative Example 1

200 mg of compound 1 and 1000 mg of D-mannitol were weighed out and mixed in an agate mortar, and the mixture was pulverized with a pestle. The mixed powder was filled into hard gelatin capsules so that the dosage can be 1.5 mg/kg based on body weight for dogs before administration, to prepare a pharmaceutical formulation.

Example 5

Solubility Evaluation Test in Water

The content of each of the pharmaceutical formulations obtained in Examples 2 to 4 and Comparative Example 1 was mixed with water, and the solubility was evaluated by measurement of concentration of compound 1 by HPLC or observation of clarity and color in the supernatant. Table 3 shows the solubility evaluation result based on measurement of concentration of compound 1 by HPLC or observation of clarity and color in each supernatant, after the content of each of the formulations obtained in Examples 2 to 4 and Comparative Example 1 (amount of compound 1 is 20 mg) was mixed with 1 to 1000 ml of purified water. According to the result for Example 2, no precipitation of compound 1 was found with mixture of water at any proportion. For Examples 3 and 4, it was found that the solubility was about 4 times and about 100 times that of Comparative Example

1.

TABLE 3

| | Solubility of each pharmaceutical formulation in water | | | |
|---|---|---|---|---|
| | Amount of water | | | |
| | 1 ml | 10 ml | 250 ml | 1000 ml |
| Example 2 | ○ | ○ | ○ | ○ |
| Example 3 | X | X | ○ | ○ |
| Example 4 | X | ○ | ○ | ○ |
| Comp. Ex. 1 | X | X | X | ○ |

In the table, the symbol x represents no dissolution of compound 1, and the symbol ○ represents complete dissolution of compound 1.

Oral Absorptivity Evaluation Test

The pharmaceutical formulations obtained in Examples 2 to 4 and Comparative Example 1 were orally administered to fasted male beagles with 20 ml of water. Approximately 2.5 ml of blood was intravenously sampled into a heparinized container at 15, 30 and 45 minutes and 1, 2, 4, 6 and 9 hours after administration, and the blood was centrifuged and the plasma was collected. The active ingredient was separated by solid phase extraction from the plasma, and the concentration was measured by high performance liquid chromatography. The result is shown in FIG. 1. Examples 2 to 4 all had higher absorptivity than the comparative example 1.

Table 4 shows the pharmacokinetic parameters for the oral administration of the pharmaceutical formulations obtained in Examples 2 to 4 and Comparative Example 1 to the fasted male beagles with 20 ml of water. Examples 2 to 4 all exhibited a higher AUC and Cmax than those of the comparative example 1, and improved absorptivity with oral administration.

TABLE 4

| | Pharmacokinetic parameters for each pharmaceutical formulation | | |
|---|---|---|---|
| Formulation | AUC0-∞ (μg · hr/ml) | Cmax (μg/ml) | Tmax (hr) |
| Example 2 | 0.82 | 0.85 | 0.67 |
| Example 3 | 0.83 | 0.52 | 1.08 |
| Example 4 | 0.92 | 0.70 | 0.75 |
| Comp. Ex. 1 | 0.31 | 0.25 | 0.42 |

The values in the table are average values with n=3.

INDUSTRIAL APPLICABILITY

Pharmaceutical solutions are prepared by dissolving a benzamide derivative or a pharmaceutically acceptable salt thereof in organic solvents and/or acidic liquids, and pharmaceutical formulations are prepared by adding surfactants, acidic substances and/or polyethylene glycols to a benzamide derivatives or a pharmaceutically aceptable salt thereof, thus providing pharmaceutical formulations with high oral absorptivity and injections, that contain as active ingredients high concentrations of benzamide derivatives or their pharmaceutically acceptable salts, which are useful as histone deacetylase inhibitors.

What is claimed is:
1. A pharmaceutical formulation comprising, a benzamide derivative represented by formula (1):

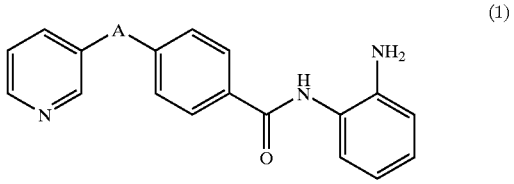

wherein A represents a structure represented by any one of the following in formula (2):

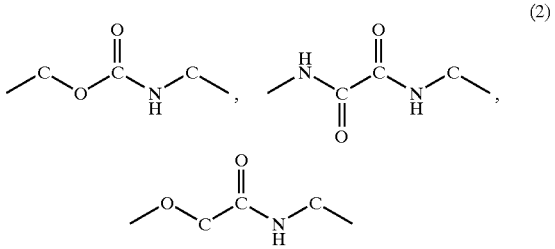

or a pharmaceutically acceptable salt thereof, and one or more than one selected from the group consisting of (1) a mixture of a polyethylene glycol and a surfactant, (2) a salt of an amino acid and a mineral acid, and (3) propylene carbonate.

2. The pharmaceutical composition according to claim 1 wherein the benzamide derivative is represented by the formula (3):

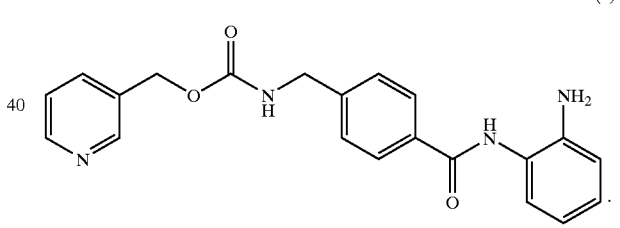

3. The pharmaceutical formulation according to claim 1, wherein the molecular weight of the polyethylene glycol is 200 to 20000.

4. The pharmaceutical formulation according to claim 1, wherein the salt of an amino acid and a mineral acid is one or more than one selected from the group consisting of glycine hydrochloride, aspartic acid hydrochloride and glutamic acid hydrochloride.

5. The pharmaceutical formulation according to claim 1, wherein the surfactant is one or more selected from anionic surfactants and nonionic surfactants.

6. The pharmaceutical formulation according to claim 5, wherein the anionic surfactant is sodium lauryl sulfate.

7. The pharmaceutical formulation according to claim 5, wherein the nonionic surfactant is one or two selected from a polyoxyethylene sorbitan fatty acid ester and a sugar ester.

8. The pharmaceutical formulation according to claim 7, wherein the polyoxyethylene sorbitan fatty acid ester is polysorbate 80.

9. The pharmaceutical formulation according to claim 7, wherein the sugar ester is a sucrose ester of fatty acid.

* * * * *